(12) United States Patent
Wagner et al.

(10) Patent No.: US 9,213,187 B2
(45) Date of Patent: Dec. 15, 2015

(54) ENGRAVED GEMSTONE VIEWER FOR PERSONAL COMMUNICATIONS DEVICES

(71) Applicant: GemEx Systems, Inc., Mequon, WI (US)

(72) Inventors: Randall Wagner, Mequon, WI (US); Kurt Schoeckert, Hartford, WI (US)

(73) Assignee: GemEx Systems, Inc., Mequon, WI (US)

( * ) Notice: Subject to any disclaimer, the term of this patent is extended or adjusted under 35 U.S.C. 154(b) by 0 days.

(21) Appl. No.: 13/901,445

(22) Filed: May 23, 2013

(65) Prior Publication Data

US 2013/0335837 A1    Dec. 19, 2013

Related U.S. Application Data

(60) Provisional application No. 61/652,072, filed on May 25, 2012.

(51) Int. Cl.
*G02B 27/02* (2006.01)
*G02B 25/00* (2006.01)
*G02B 7/02* (2006.01)

(52) U.S. Cl.
CPC ............ *G02B 27/025* (2013.01); *G02B 25/002* (2013.01); *G02B 27/027* (2013.01); *G02B 7/026* (2013.01)

(58) Field of Classification Search
CPC ... G02B 25/002; G02B 27/025; G02B 27/027
USPC .................................. 359/802, 811, 818, 819
See application file for complete search history.

(56) References Cited

U.S. PATENT DOCUMENTS

| 6,731,439 | B1 | 5/2004 | Peachee |
| 7,468,786 | B2 | 12/2008 | Wagner |
| 8,035,807 | B2 | 10/2011 | Wagner |
| 2007/0109529 | A1 | 5/2007 | Wagner et al. |
| 2009/0093274 | A1* | 4/2009 | Yamamoto ..................... 455/566 |

FOREIGN PATENT DOCUMENTS

WO    2012058641    5/2012

OTHER PUBLICATIONS

International Search Report for application PCT/US2013/042521, mailed Oct. 16, 2013.

* cited by examiner

*Primary Examiner* — William Choi
(74) *Attorney, Agent, or Firm* — Nicholas A. Kees; Godfrey & Kahn, S.C.

(57) ABSTRACT

A gemstone viewer for personal communications devices for viewing a surface of a gemstone that has been micro or nano etched, engraved or embossed with an image or inscription such as an identification number. The viewer is mounted to employ the camera and LED light source of the personal communications device. The viewer directs the light from the light source as a light beam along a path incident to the surface of the gemstone containing the inscription. The gemstone spectrally reflects the light beam along a path back toward and through a magnifying lens to the camera lens of the personal communications device thereby enhancing the magnifying properties of the camera lens to produce a viewable light image that reveals the inscription on the viewing screen of the personal communications device.

18 Claims, 6 Drawing Sheets

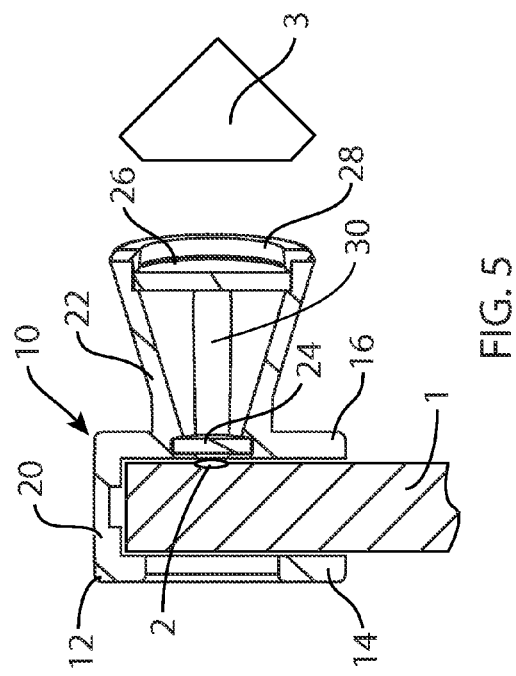
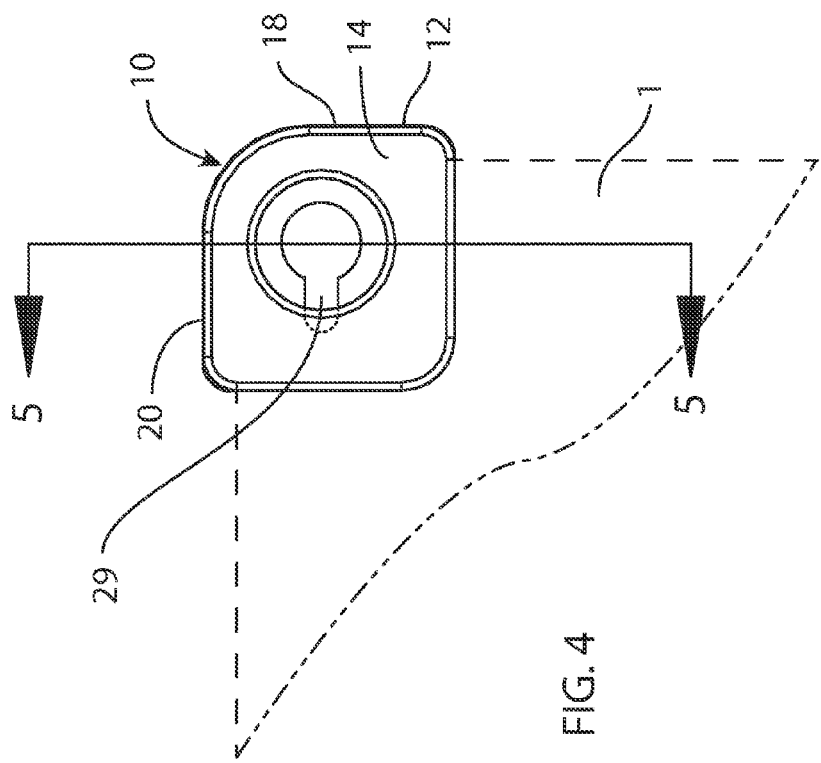

ENGRAVED GEMSTONE VIEWER FOR PERSONAL COMMUNICATIONS DEVICES

CROSS REFERENCE TO RELATED APPLICATIONS

This application claims the benefit of U.S. Provisional Patent Application Ser. No. 61/652,072, filed May 25, 2012. All of the information disclosed in that application is hereby incorporated herein by reference in its entirety.

BACKGROUND OF THE INVENTION

This invention relates to an apparatus for viewing a gemstone with an image or identification number etched into its surface.

It is known to etch a microscopic or nano-inscription on the table of the diamond using a focused ion beam. The inscription is of such a small size as to be invisible to the naked eye. The inscription is nearly impossible to read even by a skilled jeweler using a common 10× loupe because the proper viewing angle is difficult to achieve and the magnification is insufficient. The images engraved, which can include individual characters (i.e., letters and/or numbers) such as an identification number, conventionally have a length of ranging from about 300 to 1200 microns. The inscription is typically etched to a depth of about 10 to 80 nanometers. The difficulty in viewing the inscription is accentuated by the translucent nature of diamonds and other gemstones, which allows light to pass through both the ion polished area formed by the engraving process and the surrounding surface of the gemstone, (for example, the table, its top side facet).

The conventional method of viewing the inscription employed a high 65× magnification lens and camera with an electronic display screen to view the microscopic inscription. Such systems are expensive, cumbersome and complicated to use, which reduces the value of the inscription because most retailers and consumers do not have such equipment, and thus cannot see or make use of the inscription.

U.S. Pat. Nos. 7,468,786 and 8,035,807, which are incorporated by reference herein in their entirety, and invented by the same inventors as the present invention and owned by the same assignee, disclose a less expensive and more effective viewer (referred to hereinafter as an Engraved Gemstone Viewer) using the concept of illuminating the surface of the polished diamond in such a way as to create a spectral light reflection much like that of a mirror. The Engraved Gemstone Viewer is effective but lacks the convenience of being with the person at all times that engraving might be needed to be viewed, and further, lacks a way to memorize the image for later recall, comparison analysis, or remote communication of the information contained in the image.

The present invention is intended to provide solutions to these and other problems and improvements over the structures and methods described above.

SUMMARY OF THE INVENTION

The present invention pertains to an engraved gemstone viewer for viewing a surface of a gemstone that has been etched with an image, such as a brand logo or an identification number, as an accessory device that is attached to a modern personal communications device with an integrated camera, including without limitation, a tablet computer or smartphone (Apple® iPad® or iPhone®, or Samsung Android device for example). The tablet's or smartphone's camera, and its inherent digital imaging and computational functionality, are thereby inserted between the magnifying lens of the earlier Engraved Gemstone Viewer and the person observing the engraving. The gemstone may be mounted on a piece of jewelry or can remain un-mounted when received by the viewer. The integrated light source of the personal communications device (usually an LED which functions as a flash photographic light source when using the camera, but has other applications as well) is captured and directed as a beam toward a magnifying lens, which may be coated with a reflection enhancing coating, or alternatively as a beam of light directed toward the surface of the engraved diamond. If toward the lens, the lens reflects the light beam along a path incident to the surface of the gemstone containing the inscription. If toward the diamond itself, the path is likewise incident to the surface of the gemstone. In either configuration the gemstone surface reflects the light beam back along a path back to the magnifying lens, thereby producing a mirror-like reflection of the beam of light viewable to the camera lens of the personal communications device, and thereby viewable in real time on the digital display on the personal communications device. This reflection of the light off the surface of the gemstone reveals the engraved image or inscription as a differential in the reflected light, it being either brighter (reflecting) or darker (diffused) in the area engraved. Thereby the inscription is revealed in an area of the spectrally reflected light as a combination of darker and lighter planes, lines and shadows.

One advantage of the gemstone viewer for personal communications devices is the small size of the attachment device. The small size allows for convenient storage and portability making the attachment as omnipresent as the personal communications device itself. Convenience makes the viewer more practical and more likely to be used in situations where the diamond is temporarily given to a third party, such as at a jewelry store for repairs.

Another advantage of the gemstone viewer for personal communications devices is that the viewer is calibrated to correctly position the reflected image of the engraving for best viewing without making any focusing, aligning, or other adjustments to the viewer. The user is however, able to adjust and manipulate the digital image of the engraving on the viewing screen using the ordinary camera features inherent in the personal communications device. For example the user may enhance the size on the screen for better viewing or the user may take a digital photo of the image.

Another advantage of the gemstone viewer for personal communications devices is that it is an inexpensive device using a simple magnifying lens that magnifies the image to the correct degree to make the image visible in combination with the integrated lens of the personal communications device (which is not by itself powerful enough). This enables the use of the complicated and expensive electronic technology, such as camera/photographic software and digital processing software, which are embodied in the personal communications device, but otherwise prohibitively expensive for a separate gemstone viewer application.

Another advantage of gemstone viewer for personal communications devices is that the simplicity of the device allows for it to be inexpensively produced in a large number of configurations for a wide range of personal communications devices, each having different arrangements of camera lens and light sources.

A further advantage of the gemstone viewer for personal communications devices is that by conveniently removing the focusing glass piece it may also be used as a technologically enhanced "jewelers loupe" device (a low power magnifying glass) with LED lighting and further allowing the same advantage that the personal communications device camera technology gives the gemstone viewer for engraved image viewing.

A further advantage of the gemstone viewer for smartphones is with the focusing glass in place the surface of the glass correctly aligns a gemstone at the proper focal length, the "in-focus" distance from the magnifying lens, enabling a user to quickly hold the gemstone in focus while utilizing the personal communications device viewer as a technologically enhanced "jewelers loupe."

Other objects and advantages of the invention will become apparent hereinafter.

BRIEF DESCRIPTION OF THE DRAWINGS

FIG. 4 is an enlarged top plan view of the engraved gemstone viewer shown in FIG. 1, shown with a portion of the personal communications device included, shown in phantom, for positioning purposes only.

FIG. 5 is a side sectional view of the engraved gemstone viewer shown in FIG. 4, taken along line 5-5 of FIG. 4.

DESCRIPTION OF THE PREFERRED EMBODIMENTS

Figure 1:
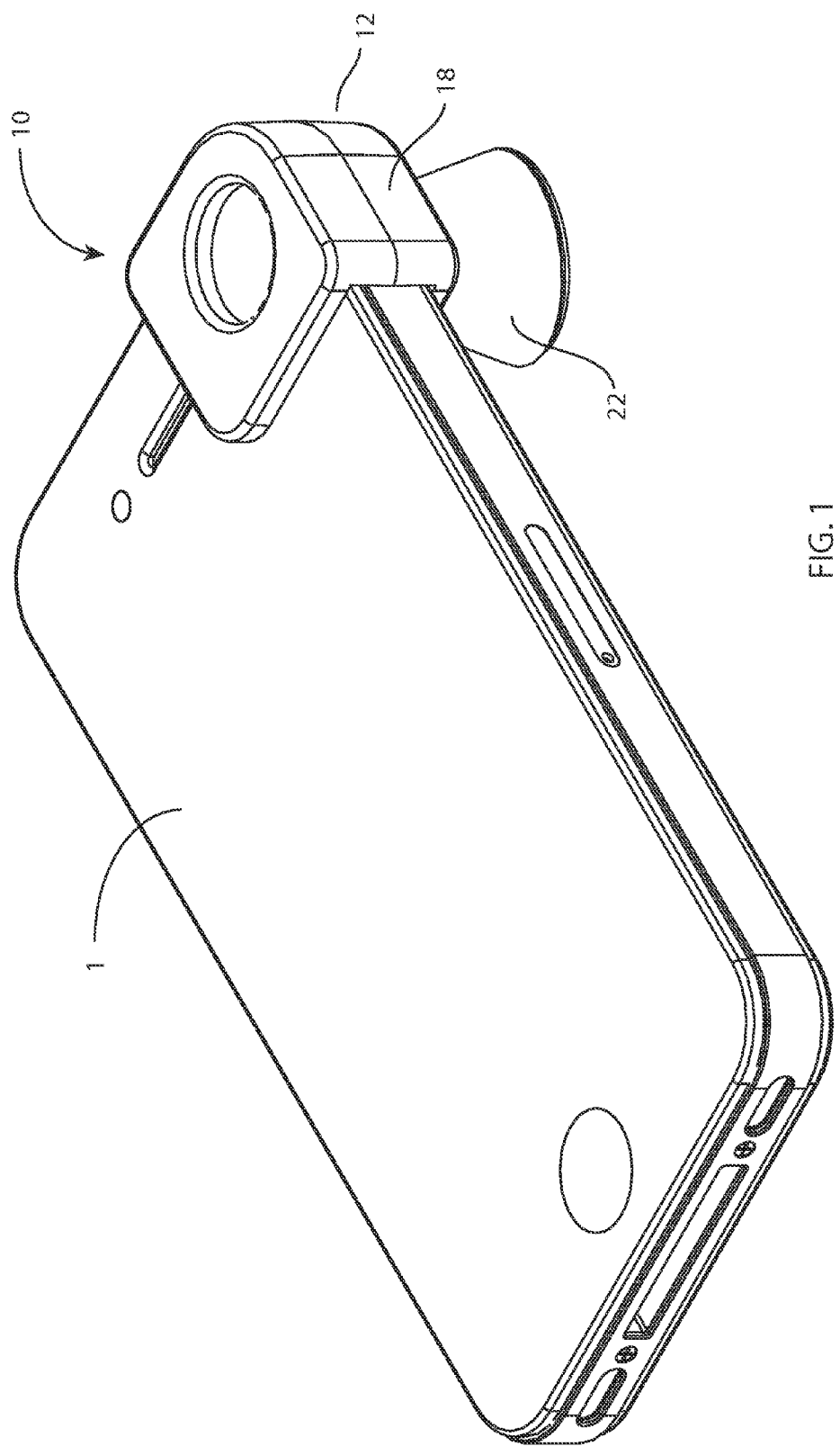
FIG. 1 is a perspective top-side view of the engraved gemstone viewer according to the present invention, mounted on an Apple® iPhone®.
Figure 2:
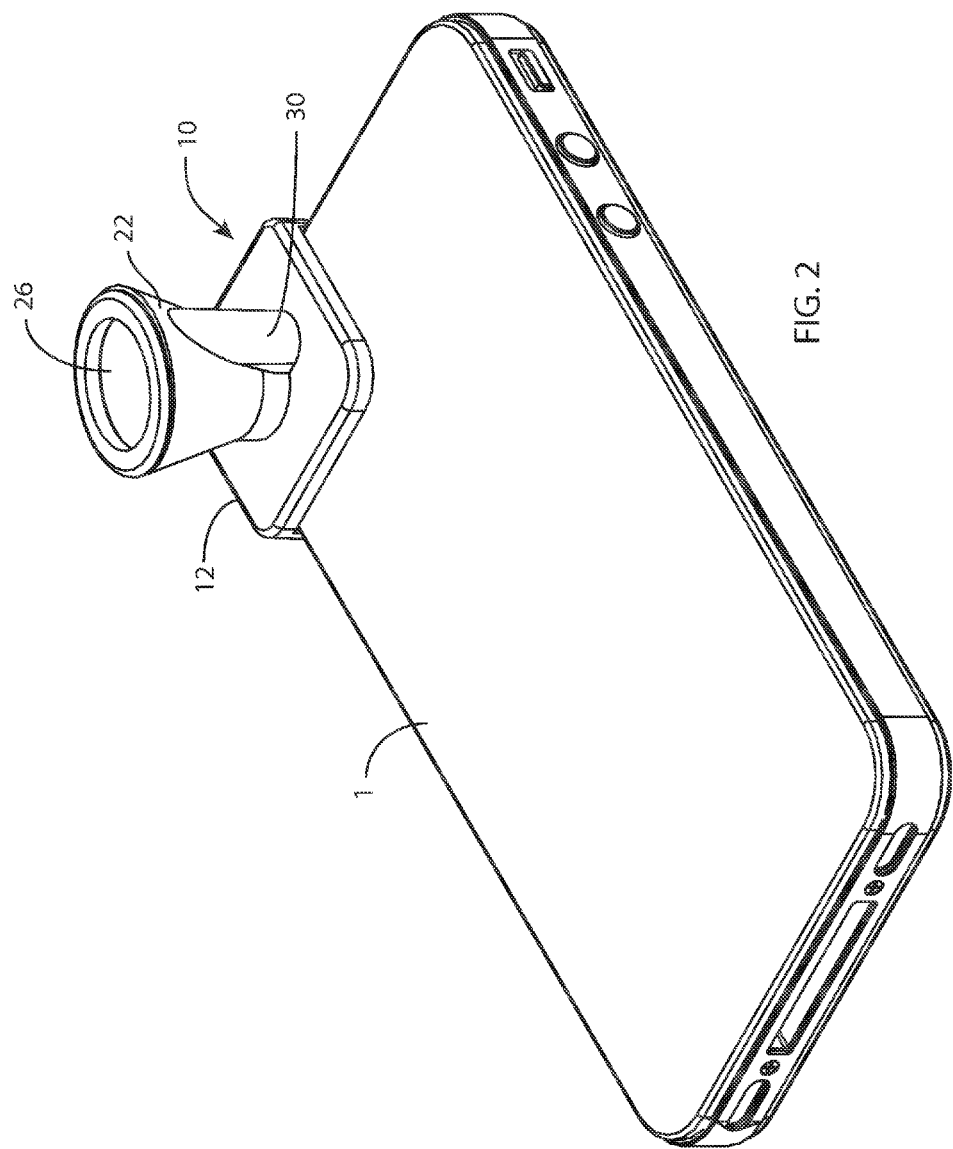
FIG. 2 is a perspective bottom-side view of the engraved gemstone viewer shown in FIG. 1, mounted on an Apple® iPhone®.
Figure 3:
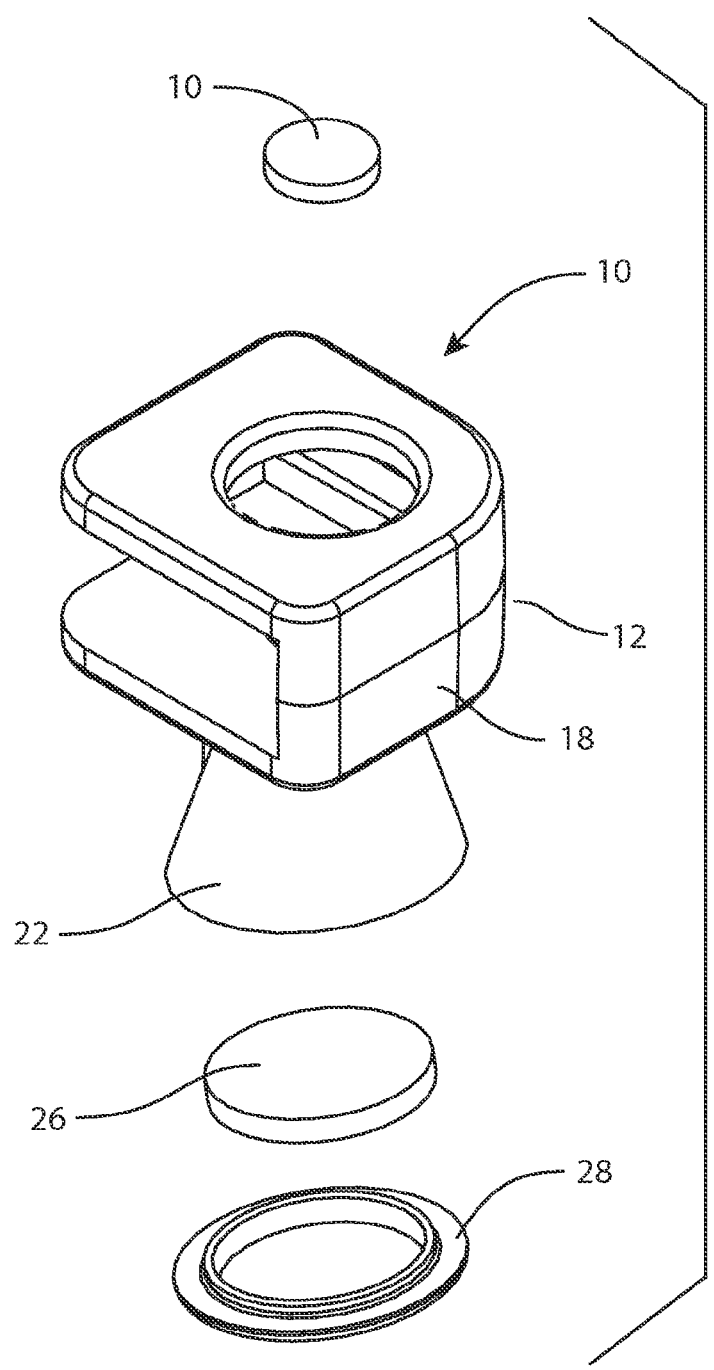
FIG. 3 is an exploded perspective view of the engraved gemstone viewer shown in FIG. 1.

The present invention generally relates to an engraved gemstone viewer 10 for personal communications device. The viewer 10 is generally shown in the drawing figures in the form of an embodiment specifically adapted to an Apple® iPhone®, although the viewer that is the subject of the invention is adaptable to be used with any smartphone, personal communications device or personal productivity device 1 with an integrated camera and a light source, such as an LED light, so as to provide photo lighting or "flash" capabilities. Such smartphone, personal communications or personal productivity devices could also include for example, a Samsung® Galaxy®, or a tablet-style computer such as an Apple® iPad®. According to the invention, the viewer 10 has a base 12 (shown generally roughly square in shape in the embodiment shown although many other shapes would function equally well) to receive the corner of a personal communications device 1 where the camera lens and light source are positioned on the back side of the personal communications device. In the embodiment shown, the base 12 has a top plane 14 and bottom plane 16 spaced apart by two adjoining side planes 18, 20, which preferably is formed unitarily but may as well be formed of parts and assembled. The base 12 is open on the opposing two adjoining sides so as to accommodate the thickness of the personal communications device 1 that is received through the two open sides. Preferably the top plane 14, bottom plane 16 and two side planes 18, 20 of the base 12 are precisely spaced so as to make frictional contact with the personal communications device 1, to thereby secure the viewer 10 to the personal communications device without applying additional pressure or mechanical means. In alternative embodiments of the viewer 10, the base 12 may have a different shape and size so as to correctly orient the device to receive a different model of smartphone or personal communications device, with the camera lens and light source in respectively different positions based on the positioning of the equipment in the personal communications device.

A viewer body 22, shown to have a funnel shape in this embodiment, is attached to or formed integrally with the bottom plane 16, and projects away from personal communications device 1. The viewer body 22 is a structure sized to accommodate a magnifying lens 24 generally at the level of the bottom plane 16, and generally coaxially aligned with but not contacting the lens 2 of the camera or body of the personal communications device 1. The bottom plane 16 is open to allow an unobstructed path for light to pass through the magnifying lens 24 to the lens 2 of the camera of the personal communications device 1. The magnifying lens 24 is of such a calibration as to visually enlarge objects in the view of the camera of the personal communications device 1 beyond that which is otherwise possible by the unaided lens of the camera itself.

Figure 7:
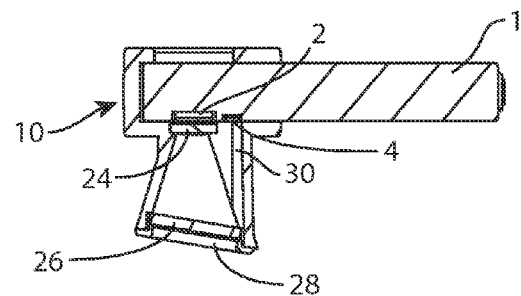
FIG. 7 is a side sectional view of the engraved gemstone viewer for smartphones shown in FIG. 6, taken along line 7-7 of FIG. 6.
Figure 6:
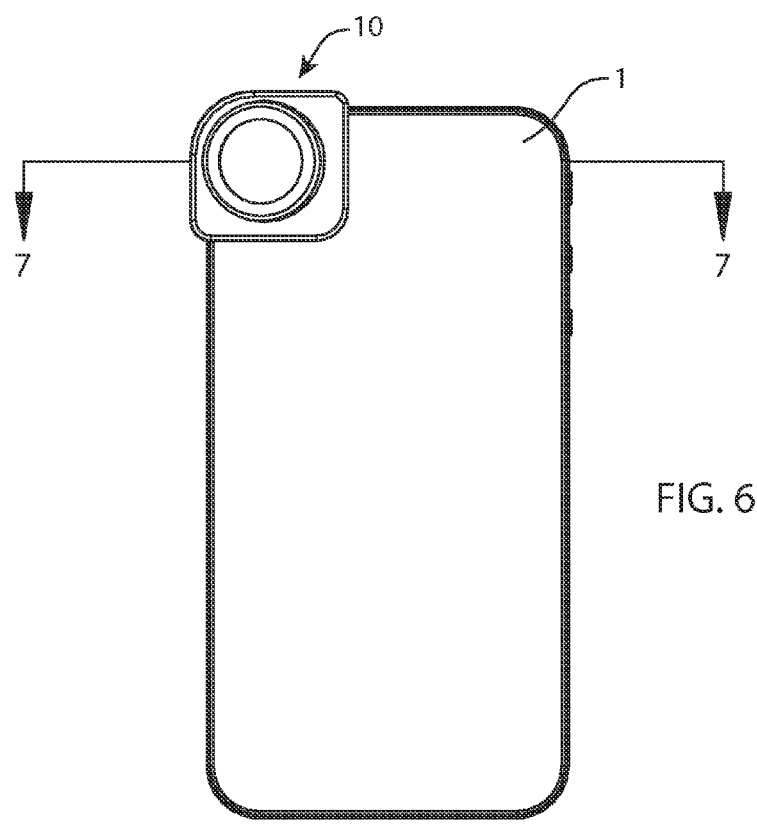
FIG. 6 is a bottom plan view of the engraved gemstone viewer shown in FIG. 1, mounted on an Apple® iPhone®.
Figure 9:
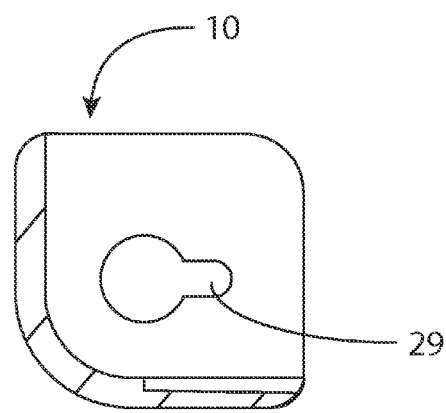
FIG. 9 is a side sectional view of the engraved gemstone viewer shown in FIG. 8, taken along line 9-9 of FIG. 8.
Figure 8:
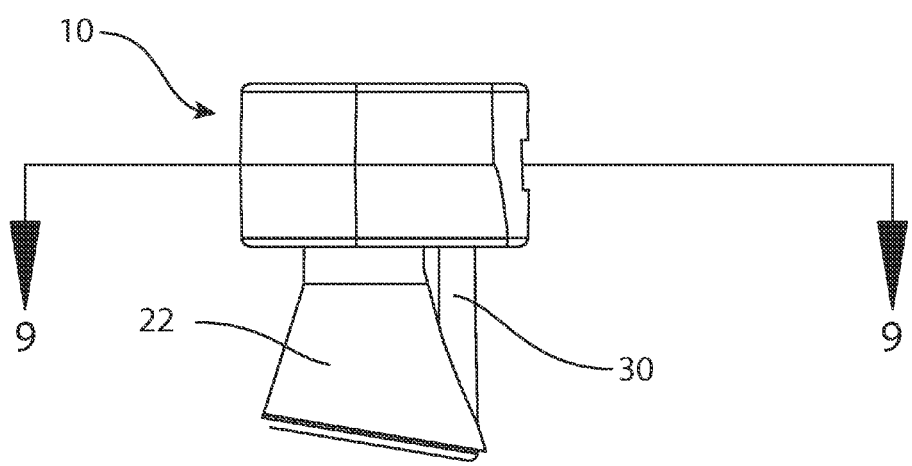
FIG. 8 is a side view of the engraved gemstone viewer.

As shown in more detail in FIGS. 6-9, the opposite end of the viewer body 22 terminates at a plane, generally not parallel to the plane of the magnifying lens, where a focusing glass 26 is removably held in place by a removable retaining ring 28. The focusing glass 26 and the magnifying lens 24 are held at the correct distance from each other by the viewer body 22 such that the camera of the personal communications device 1 is properly focused through the magnifying lens at the top of the viewer body to the surface of a gemstone 3 (FIG. 5), such as a diamond, placed against the outside surface of the focusing glass at the bottom of the viewer body. The optimal angle for the plane of the focusing glass 26 compared to the plane of the magnifying lens 24 is determined by the focal length of the magnifying lens in relation to the location of the light source 4. In this embodiment, the angle would be between about 5 degrees and 25 degrees, and most preferably about 13 to 16 degrees.

The bottom plane 16 of the base 12 also has an opening 29 leading to a channel 30 to allow an unobstructed path for light from the light source 4 of the personal communications device 1 to pass through channel 30 oriented toward the focusing glass 26. As described above, then, the focusing glass 26 is oriented at an angle so the diamond 3 making contact with the focusing glass will receive the light beam path as directed to it from the light source 4 and reflect the light beam path back to, and through, the magnifying lens 24 to the camera lens 2 of the personal communications device 1.

In alternative embodiments, the path of the light source 4 could be oriented toward the magnifying lens so that the path of the light from the light source leads to the magnifying lens and then to the surface of the diamond 3, which in turn reflects the path of light back to, and through, the magnifying lens 24 to the lens 2 of the camera of the personal communications device. Such oriented paths of light beams, and the angles required, are disclosed in the Engraved Gemstone Viewer patents as referenced above.

While this invention is susceptible of embodiment in many different forms, the drawings show and the specification describes only some of the preferred embodiments of the invention. It should be understood that the drawings and specification are to be considered an exemplification of the principles of the invention. They are not intended to limit the broad aspects of the invention to the embodiments illustrated. That function is left to the claims, which follow.

We claim:

1. A device for use with an electronic communications device for viewing a gemstone to reveal a mark or inscription, such as an image or an identification number, engraved, embossed or etched into the gemstone's surface, the electronic communications device having a camera lens, the device comprising:
   a base;
   a viewer body, connected to or formed integrally with the base;
   a magnifying lens connected to the viewer body; and
   a focusing glass connected to the viewer body, with the magnifying lens positioned between the focusing glass and the camera lens;
   the focusing glass and the magnifying lens being held at a sufficient distance from each other by the viewer body such that the camera lens is properly focused through the magnifying lens to the surface of the gemstone when the surface of the gemstone is placed against the focusing glass.

2. A device as recited in claim 1 wherein the magnifying lens is connected to the base generally coaxially aligned with but not contacting the camera lens.

3. A device as recited in claim 2 wherein the electronic communications device includes a light source, and wherein the base has an opening to allow an unobstructed light beam path for light from the light source to pass through a channel oriented toward the focusing glass.

4. A device as recited in claim 3 wherein the focusing glass is oriented so the gemstone, in making contact with the focusing glass, will be in the light beam path as directed to the gemstone from the light source, and will reflect the light beam along a path back to, and through, the magnifying lens to the camera lens.

5. A device a recited in claim 4 where the focusing glass is held in place by a removable retaining ring, which allows the focusing glass to be removed and installed.

6. A device as recited in claim 5 wherein the focusing glass is held at an angle of about 5 degrees to about 25 degrees with respect to the magnifying lens.

7. A device as recited in claim 6 wherein the focusing glass is held at an angle of about 13 degrees to about 16 degrees with respect to the magnifying lens.

8. A device as recited in claim 2 further comprising a light source, and wherein the base has an opening to allow an unobstructed light beam path for light from the light source to pass through a channel oriented toward the focusing glass.

9. A device as recited in claim 8 wherein the focusing glass is oriented so the gemstone, in making contact with the focusing glass, will be in the light beam path as directed to the gemstone from the light source, and will reflect the light beam along a path back to, and through, the magnifying lens to the camera lens.

10. A device as recited in claim 9 wherein the base includes a top plane and bottom plane spaced apart from each other by two adjoining side planes, and wherein the top plane, bottom plane and two side planes are precisely spaced to make contact with the electronic communications device so as to secure the base to the electronic communications device mainly by friction without applying additional pressure or mechanical means.

11. A device a recited in claim 10 where the focusing glass is held in place by a removable retaining ring, which allows the focusing glass to be removed and installed.

12. A device as recited in claim 11 wherein the focusing glass is held at an angle of about 5 degrees to about 25 degrees with respect to the magnifying lens.

13. A device as recited in claim 12 wherein the focusing glass is held at an angle of about 13 degrees to about 16 degrees with respect to the magnifying lens.

14. A device for use with an electronic communications device for viewing a gemstone to reveal a mark or inscription, such as an image or an identification number, engraved, embossed or etched into the gemstone's surface, the electronic communications device having a camera lens and a light source, the device comprising:
   a base, including a top plane and bottom plane spaced apart from each other by two adjoining side planes;
   a viewer body, connected to or formed integrally with the base;
   a magnifying lens connected to the viewer body; and
   a focusing glass connected to the viewer body, with the magnifying lens positioned between the focusing glass and the camera lens;
   the focusing glass and the magnifying lens being held at a sufficient distance from each other by the viewer body such that the camera lens is properly focused through the magnifying lens to the surface of the gemstone when the surface of the gemstone is placed against the focusing glass.

15. A device as recited in claim 14 wherein the bottom plane has an opening to allow an unobstructed light beam path for light from the light source to pass through a channel oriented toward the focusing glass.

16. A device as recited in claim 15 wherein the top plane, bottom plane and two side planes are precisely spaced to make contact with the electronic communications device so as to secure the base to the electronic communications device mainly by friction without applying additional pressure or mechanical means.

17. A device a recited in claim 16 where the focusing glass is held in place by a removable retaining ring, which allows the focusing glass to be removed and installed.

18. A device as recited in claim 17 wherein the focusing glass is held at an angle of about 5 degrees to about 25 degrees with respect to the magnifying lens.

* * * * *